United States Patent [19]

Baum et al.

[11] Patent Number: 4,942,164

[45] Date of Patent: Jul. 17, 1990

[54] POLYFLUORINATED DIISOCYANATES AND FLUORINATED POLYURETHANES PREPARED THEREFROM

[75] Inventors: Kurt Baum, Pasadena; Aslam A. Malik, San Dimas; Donald D. Tzeng, San Jose, all of Calif.

[73] Assignee: Fluorochem Inc., Azusa, Calif.

[21] Appl. No.: 350,130

[22] Filed: May 8, 1989

[51] Int. Cl.$^5$ ............................................. C08G 18/77
[52] U.S. Cl. ..................................... 528/70; 560/356
[58] Field of Search .......................... 528/70; 560/356

[56] References Cited

U.S. PATENT DOCUMENTS 3,657,306  4/1972  Murray ................................ 560/356

*Primary Examiner*—Maurice J. Welsh
*Attorney, Agent, or Firm*—John H. Crowe

[57] ABSTRACT

Polyfluorinated diisocyanates having the formula $OCN-CH_2CH_2-(CF_2)_n-CH_2CH_2-NCO$, in which n is a whole number from 2 to 16, inclusive, and their analogous monofunctional isocyanates having the formula $F(CF_2)_n-CH_2CH_2-NCO$, wherein n is a whole number from 1 to 20, inclusive. The polyfluorinated diisocyanates react with polyfluorinated diols having the formula $HO-CH_2CH_2-(CF_2)_n-CH_2CH_2-OH$, wherein n is a whole number of from 1 to 20, inclusive, to form useful fluorinated polyurethanes.

13 Claims, No Drawings

POLYFLUORINATED DIISOCYANATES AND FLUORINATED POLYURETHANES PREPARED THEREFROM

The Government has rights in this invention pursuant to Contracts N00014-84-C-0388 and N00014-88-C-0150 awarded by the Department of the Navy.

BACKGROUND OF THE INVENTION

This invention relates generally to polyfluorinated diisocyanates and a method of synthesizing them. More particularly, the invention relates to such diisocyanates defined by the formula $OCN-CH_2CH_2-(CF_2)_n-CH_2CH_2-NCO$, wherein n is a whole number of from 2 to 16, inclusive.

Diisocyanates are known to be useful for the preparation of polyurethanes and polyureas, and fluorocarbon segments are known to generally impart favorable dielectric, water-repellency and anti-fouling properties to polymer systems. The synthesis of the perfluoroalkylene diisocyanates $OCN-(CF_2)_n-NCO$ by the Curtius rearrangement of the corresponding acyl azides has been reported—Knunyants, I. L.; Krasuskaya, M. P.; Del'tsova, D. P. *Izv. Akad, Nauk SSSR, Ser. Khim.*, Engl. Ed., 1066 (1966). Reactions of these isocyanates with alcohols give urethanes including and characterized by the structure $-CF_2-NH-CO_2R$. Compounds with NH groups adjacent to CF groups generally have a tendency toward instability because of the elimination of HF. The synthesis of tetrahydroperfluoroalkylene diisocyanates, $OCN-CH_2-(CF_2)_n-CH_2-NCO$, has also been reported. See Takakura, T.; Yamabe, M.; and Kato, M., *Nippon Kagaku Kaishi*, 2208 (1985), where the method of synthesis involved the Curtius rearrangement of the corresponding acid azides.

The most commonly used method for the synthesis of commercially important isocyanates is the reaction of phosgene with amines or amine salts. See Babad, H.; Zeiler, A. G., *Chem. Rev.*, 73, 75 (1973) and Farlow, M. S., *Org. Syn.*, Coll. Vol. IV, 521. The amine reacts with phosgene to yield the corresponding carbamoyl chloride which then loses hydrogen chloride to form the isocyanate.

SUMMARY OF THE INVENTION

We have now, by this invention, provided a series of novel polyfluorinated diisocyanates and a novel method of synthesizing them employing, as starting materials, perfluoroalkylene bis(ethylamines) having the formula $NH_2-CH_2CH_2-(CF_2)_n-CH_2CH_2-NH_2$, wherein n is a whole number of from 2 to 16, inclusive. Such diamines, and their method of preparation are described in copending U.S. patent application No. 07/202,505, filed June 6, 1987, by Paul G. Cheng and one of the present applicants (Baum), which is a division of U.S. patent application No. 07/020,361, filed Mar. 2, 1987, now abandoned. While the focus of that application is on diamines in which the range of n values is from 4 through 16, we have made the precursor diiodide for use in the diamine preparation procedure of the application in which n is 2, and there is no reason to doubt that the corresponding diamine can be produced therefrom by said procedure. In the present work, diamines in which n varied from 4 through 12 were converted to their hydrochloride salts by bubbling gaseous hydrogen chloride into suspensions of the diamines in a suitable solvent. Phosgene was then introduced at temperatures up to 130° C. to form the diisocyanates. The products were purified by distillation or sublimation, and yields of from 55 to 86% were obtained. Efficient stirring was required because of the heterogenous nature of the reaction. 1,2-Dichlorobenzene was used as the solvent because of its convenient boiling point, but any of a number of other organic solvents unreactive with phosgene could be used as well. The solvent should preferably be sufficiently high-boiling to drive off HCl at reflux at an acceptable rate, although low-boiling solvents are suitable for use in pressure reactors. The reaction of this invention can also be used to obtain the analogous monofunctional isocyanates having the formula $F(CF_2)_n-CH_2CH_2-NCO$ in which n varies from 1 through 20, inclusive. These monofunctional isocyanates can be employed to impart water-repellency to textiles.

We have reacted diisocyanates in accordance with this invention with diols to obtain polyurethanes, as will be described in greater detail in examples below. In general any diol can be used in this polyurethane reaction, but the ones we employed in our work were those having the general formula $HO-CH_2CH_2-(CF_2)_n-CH_2CH_2-OH$. Such diols in which n is a whole number of from 1 to 20, inclusive, have been disclosed in a Japanese patent (Asahi Glass Co., Ltd., Jpn. Koka; Tokkyo Koho J P 82, 99, 552, 21 June 1982). Polyureas can be obtained by reaction of the diisocyanates of this invention with diamines.

It is thus a principal object of the present invention to provide novel polyfluroinated diisocyanates from which polyurethanes with good dielectric, water-repellency and anti-fouling properties can be made.

Another object of the invention is to provide such diisocyanates suitable for the synthesis of polyureas with good dielectric, water-repellency and anti-fouling properties.

Still another object of the invention is to provide a novel method of synthesizing such diisocyanates.

A further object of the invention is to provide novel monofunctional isocyanates useful for imparting water-repellency to textiles.

An additional object of the invention is to provide means for synthesizing the above-mentioned polyurethanes.

Other objects, features and advantages of the invention will be apparent to those skilled in the art in the light of the present teachings.

DESCRIPTION OF THE PREFERRED EMBODIMENTS

To more fully flesh out the description of this invention, the following examples are presented. It is to be understood, however, that these examples are offered merely as a means of illustration and are not intended to limit the scope of the invention to the particular combinations of materials, conditions, proportions, etc., set forth therein.

EXAMPLE I

Preparation of 3,3,4,4,5,5,6,6-Octafluorooctane-1,8-diisocyanate

Hydrogen chloride gas was bubbled into a stirred solution of 1,8-diamino-3,3,4,4,5,5,6,6-octafluorooctane (25 g, 86.8 mmol) in 1,2-dichlorobenzene (315 mL) at a rate of 10 mL/min for 1.5 hours. Phosgene was then bubbled into the mixture and the temperature was raised gradually to 130° C. The formation of a homogeneous solution indicated completion of the reaction. Phosgene was flushed from the reaction mixture with argon, and the solvent was removed by distillation (30°–32° C./0.2 mm). The residue was distilled (110° C./0.3 mm) to give 25.4 g (86%) of 3,3,4,4,5,5,6,6-octafluorooctane-1,8-diisocyanate, a colorless liquid: Glc (OV—17, 120° C. to 280° C. at 16° C./min) $R_T$ 6.7 min; $^1$H NMR (CDCl$_3$) δ 3.66 (t, J=6.9 Hz, 4H) and 2.40 (tt, J=17.9 Hz and 6.9 Hz, 4H); $^{19}$F NMR (CDCl$_3$) φ 114.84 (4F) and 123.93 (4F); IR (CH$_2$Cl$_2$) 3150, 3050, 2300, 1360–1100 and 1020 cm$^{-1}$. Anal. Calcd for C$_{10}$H$_8$F$_8$N$_2$O$_2$: C, 35.29; H, 2.35; F, 44.71; N, 8.24. Found: C, 35.36; H, 2.44; F, 44.56; N, 8.12.

EXAMPLE II

Preparation of 3,3,4,4,5,5,6,6,7,7,8,8-Dodecafluorodecane-1,10-diisocyanate

Hydrogen chloride gas was bubbled into a stirred solution of 1,10-diamino-3,3,4,4,5,5,6,6,7,7,8,8-dodecafluorodecane (5.0 g, 12.9 mmol) in 1,2-dichlorobenzene (75 mL) at a rate of 10 mL/min for 1.5 hours. Phosgene was then bubbled into the mixture and the temperature was raised gradually to 130° C. When a homogeneous solution was obtained phosgene was flushed from the reaction mixture with argon, and the solvent was removed by distillation (30°–32° C./0.2 mm). The residue was distilled (115° C./0.2 mm) to give 4.5 g (80%) of 3,3,4,4,5,5,6,6,7,7,8,8-dodecafluorodecane-1,10-diisocyanate, a white waxy solid; mp 30°–31° C. (hexane); $^1$H NMR (CDCl$_3$) δ 3.67 (t, J=6.9 Hz, 4H) and 2.42 (tt, J=18.0 Hz and 6.9 Hz, 4H); $^{19}$F NMR (CDCl$_3$) φ 114.76 (4F), 122,08 (4F) and 124.04 (4F); IR (CF$_2$Cl$_2$) 3100, 3050, 2300, and 1380–1110 cm$^{-1}$. Anal. Calcd. for C$_{12}$H$_8$F$_{10}$N$_2$O$_2$: C, 32.74; H, 1.83; F, 51.79; N, 6.36. Found: C, 32.52; H, 1.81; F, 52.01; N, 6.45.

EXAMPLE III

Preparation of 3,3,4,4,5,5,6,6,7,7,8,8,9,9,10,10-hexadecafluorodecane-1,12-diisocyanate Hydrogen chloride gas was bubbled into a stirred solution of 1,12-diamino-3,3,4,4,5,5,6,6,7,7,8,8,9,9,10,10-hexadecafluorodecane (4.1 g, 8.4 mmol) in 1,2-dichlorobenzene (100 mL) at a rate of 10 mL/min for 1.5 hours. Phosgene was then bubbled into the mixture and the temperature was raised gradually to 130° C. When a clear homogeneous solution was obtained, phosgene was flushed from the reaction mixture with argon, and the solvent was removed by distillation (30°–32° C./0.2 mm). The residue was recrystallized from hexane to give 2.5 g (55%) of 3,3,4,4,5,5,6,6,7,7,8,8,9,9,10,10-hexadecafluorodecane-1,12-diisocyanate, a white waxy solid: mp 86°–88° C.; $^1$H NMR (CDCl$_3$) δ 3.68 (t, J=6.9 Hz, 4H) and 2.42 (tt, J=18.0 Hz and 6.9 Hz, 4H) $^{19}$F NMR (CDCl$_3$) φ 114.86 (4F), 122.29 (8F) and 124.07 (4F); IR (CH$_2$Cl$_2$),, 3100, 3050, 2350, 1420, 1340–1050, and 900 cm$^{-1}$. Anal. Calcd for C$_{14}$H$_8$F$_{16}$N$_2$O$_2$: C, 31.13; H, 1.49; N, 5.19; F, 56,27. Found: C, 31.03; H, 1.47; N, 4.98; F, 56.38.

EXAMPLE IV

Preparation of 3,3,4,4,5,5,6,6,7,7,8,8,9,9,10,10,11,11,12,12,12-heneicosafluorododecyl Isocyanate Hydrogen chloride gas was bubbled into a stirred solution of 1-amino-3,3,4,4,5,5,6,6,7,7,8,8,9,9,10,10,11,11,12,12,12-heneicosafluorododecane (0.60 g, 1.06 mmol) in 1,2-dichlorobenzene (100 mL) at a rate of 10 mL/min for 3 hours. Phosgene was then bubbled into the mixture and the temperature was raised gradually to 130° C. After a clear homogeneous solution was obtained (4 hours), phosgene was flushed from the reaction mixture with argon and the solution was filtered. Solvent was removed by distillation (30°–32° C./0.2 mm) and the residue was crystallized from hexane to give 0.21 g (33.6%) of 3,3,4,4,5,5,6,6,7,7,8,8,9,9,10,10,11,11,12,12,12-heneicosafluorododecyl isocyanate, a white solid: mp 70°–71° C.; $^1$H NMR (CDCl$_3$) δ 3.65 (t, J=7 Hz, 2H) and 2.40 (tt, J=7 Hz and 17 Hz, 2H); $^{19}$F NMR (CDCl$_3$) φ 81.7 (3F), 115.3 (2F), 122.6 (10F), 123.6 (2F), 124.4 (2F) and 127.0 (2F); IR (CH$_2$Cl$_2$) 2375, 1230–1140, and 1050 cm$^{-1}$. Anal. Calcd for C$_{13}$H$_4$F$_{21}$NO: C, 26.50; H, 0.68; F, 67.71; N, 2.39. Found: C, 26.36; H, 0.67; F, 67.45; N, 2.39.

EXAMPLE V

Preparation of Polyurethane from 3,3,4,4,5,5,6,6-Octafluorooctane-1,8-Diisocyanate and 1,8-Dihydroxy-3,3,4,4,5,5,6,6-octafluorooctane A mixture of 3,3,4,4,5,5,6,6-octafluorooctane-1,8-diisocyanate (3,008 g, 8.842 mmol) and 1,8-dihydroxy-3,3,4,4,5,5,6,6-octafluorooctane (2.566 g, 8.843 mmol) was heated at 45° C. to form a homogeneous mixture. Dibutyltin (IV) dilaurate (10 μL of 0.084M solution in dichloromethane) was added and the mixture was heated at 45° C. for 4 h. The product, a white solid, was further cured at 50° C. for 4 h, 70° C. for 3 h and 85° C. for 2 h. The polymer (5.5 g, 99%) was soluble in boiling acetone, boiling ethyl acetate and hot (70° C.) DMF. The material melted at 135°–145° C. and underwent decomposition at ca. 300° C.; IR (thin film) 3350, 3025, 1700, 1540 and 1340–1050 cm$^{-1}$; inherent viscosity 0.141 (DMF, 30° C., 0.265 g/100 ml).

EXAMPLE VI

Preparation of Polyurethane from 3,3,4,4,5,5,6,6,7,7,8,8-Dodecafluorodecane-1,10-diisocyanate and 1,8-Dihydroxy-3,3,4,4,5,5,6,6-octafluorooctane A mixture of 3,3,4,4,5,5,6,6,7,7,8,8-dodecafluorodecane-1,10-diisocyanate (489.8 mg, 1.112 mmol) and 1,8-dihydroxy-3,3,4,4,5,5,6,6-octafluorooctane (322 mg, 1.110 mmol) was heated at 45° C. to form a homogeneous mixture. Dibutyltin dilaurate (5 μL of 0.084M solution in dichloromethane) was added and the mixture was heated at 45° C. for 3 hours. The resulting white solid was further cured at 50° C. for 2.5 hours, 75° C. for 2 hours, and 85° C. for 1 hour. The polymer was soluble in boiling acetone and hot (70° C.) DMF: mp 130°–145° C.; IR (thin film) 3440, 3050, 1700, 1540 and 1360–1050 cm$^{-1}$; inherent viscosity 0.377 (DMF, 30° C., 0.257 g/100 ml).

EXAMPLE VII

Preparation of Polyurethane from 3,3,4,4,5,5,6,6-Octafluorooctane-1,8-diisocyanate and 1,6-Dihydroxy-3,3,4,4-tetrafluorohexane A mixture of 3,3,4,4,5,5,6,6-octafluorooctane-1,8-diisocyanate (350 mg, 1.029 mmol) and 1,6-dihydroxy-3,3,4,4-tetrafluorohexane (195.5 mg, 1.028 mmol) was heated at 40° C. to form a homogeneous mixture. Dibutyltin dilaurate (5 μL of 0.086M solution in dichloromethane) was added and the mixture was heated at 45° C. for 2.5 hours. The product, a white solid, was further cured at 50° C. for 2 hours, 70° C. for 2.5 hours, and 85° C. for 1 hour. The polymer (0.529 g, 97%) was soluble in boiling acetone and hot (70° C.) DMF: mp 155°–165° C.; IR (thin film) 3450, 3050, 1700, 1550 and 1360–1050 cm$^{-1}$; inherent viscosity 0.113 (DMF, 30° C., 0.262 g/100 ml).

EXAMPLE VIII

Preparation of Polyurethane from 3,3,4,4,5,5,6,6,7,7,8,8-Dodecafluorodecane-1,10-diisocyanate and 1,10-Dihydroxy-3,3,4,4,5,5,6,6,7,7,8,8-dodecafluorodecane A mixture of 3,3,4,4,5,5,6,6,7,7,8,8-dodecafluorodecane-1,10-diisocyanate (587.0 mg, 1.50 mmol) and 1,10-dihydroxy-3,3,4,4,5,5,6,6,7,7,8,8-dodecafluorodecane (662 mg, 1.50 mmol) was heated at 75° C. for 30 min to form a homogeneous mixture. Dibutyltin dilaurate (5 μL of 0.23M solution in dichloromethane) was added and the mixture was heated at 75° C. for 2 hours. The temperature was raised to 93° C. over 4 hours and then maintained at 93° C. for an additional 2 hours. The polymer, a white brittle solid, was soluble in boiling acetone, boiling ethyl acetate and hot (ca 75° C.) DMF: mp 130°–142° C.; IR (KBr) 3400, 3000, 1710, 1530, and 1100–1300 cm$^{-1}$; inherent viscosity 0.133 (DMF, 30° C., 0.253 g/100 ml).

EXAMPLE IX

Preparation of Polyurethane from 3,3,4,4,5,5,6,6,7,7,8,8,9,9,10,10-Hexadecafluorododecane-1,12-diisocyanate and 1,12-dihydroxy-3,3,4,4,5,5,6,6,7,7,8,8,9,9,10,10-hexadecafluorodecane A mixture of 1.16 g (2.15 mmol) of 3,3,4,4,5,5,6,6,7,7,8,8,9,9,10,10-Hexadecafluorodecane-1,12-diisocyanate and 1.05 g (2.15 mmol) of 1,12-dihydroxy-3,3,4,4,5,5,6,6,7,7,8,8,9,9,10,10-hexadecafluorodecane was sealed in a glass tube and heated at 175° C. for 16 hours. A polymeric rod was obtained. The material melted at 135° C. and showed a DTA exotherm at 320° C.

While selected embodiments of our invention have been described in detail herein, it should be understood that the invention is not limited to those specific embodiments but is broad enough in concept to include modifications thereof within its parameters as taught herein and defined by the language of the following claims.

We claim:

1. As a composition of matter, a polyfluorinated diisocyanate having the formula OCN—CH$_2$CH$_2$—(CF$_2$)$_n$—CH$_2$CH$_2$—NCO, wherein n is a whole number of from 2 to 16, inclusive.

2. A composition of matter in accordance with claim 1 in which n is 4, 6, 8 or 10.

3. As a composition of matter, a polyfluorinated monoisocyanate having the formula F(CF$_2$)$_n$—CH$_2$CH$_2$—NCO, wherein n is a whole number of from 1 to 20, inclusive.

4. A composition of matter in accordance with claim 3 in which n is 10.

5. A fluorinated polyurethane composition comprising the polymerization product of at least one compound selected from the group consisting of polyfluorinated diisocyanates having the formula OCN—CH$_2$CH$_2$—(CF$_2$)$_n$—CH$_2$CH$_2$—NCO, wherein n is a whole number of from 2 to 16, inclusive, and at least one diol.

6. A fluorinated polyurethane composition in accordance with claim 5 in which said at least one diol is selected from the group consisting of polyfluorinated diols having the formula HO—CH$_2$CH$_2$—(CF$_2$)$_n$—CH$_2$CH$_2$—OH, wherein n is a whole number of from 1 to 20, inclusive.

7. A fluorinated polyurethane composition in accordance with claim 6 in which the polyfluorinated diisocyanates are those wherein n is 4, 6, 8 or 10, respectively.

8. A fluorinated polyurethane composition in accordance with claim 7 in which the polyfluorinated diols are those wherein n is 2, 4, 6 or 8, respectively.

9. A fluorinated polyurethane composition in accordance with claim 8 in which the at least one polyfluorinated diisocyanate compound is 3,3,4,4,5,5,6,6-octafluorooctane-1,8-diisocyanate and the at least one polyfluorinated diol is 1,8-dihydroxy-3,3,4,4,5,5,6,6-octafluorooctane.

10. A fluorinated polyurethane composition in accordance with claim 8 in which the at least one polyfluorinated diisocyanate compound is 3,3,4,4,5,5,6,6,7,7,8,8-dodecafluorodecane-1,10-diisocyanate and the at least one polyfluorinated diol is 1,8-dihydroxy-3,3,4,4,5,5,6,6-octofluorooctane.

11. A fluorinated polyurethane composition in accordance with claim 8 in which the at least one polyfluorinated diisocyanate compound is 3,3,4,4,5,5,6,6-octafluorooctane-1,8-diisocyanate and the at least one polyfluorinated diol is 1,6-dihydroxy-3,3,4,4-tetrafluorohexane.

12. A fluorinated polyurethane composition in accordance with claim 8 in which the at least one polyfluorinated diisocyanate compound is 3,3,4,4,5,5,6,6,7,7,8,8-dodecafluorodecane-1,10-diisocyanate and the at least one polyfluorinated diol is 1,10-dihydroxy-3,3,4,4,5,5,6,6,7,7,8,8-dodecafluorodecane.

13. A fluorinated polyurethane composition in accordance with claim 8 in which the at least one polyfluorinated diisocyanate compound is 3,3,4,4,5,5,6,6,7,7,8,8,9,9,10,10-hexadecafluorododecane-1,12-diisocyanate and the at least one polyfluorinated diol is 1,12-dihydroxy-3,3,4,4,5,5,6,6,7,7,8,8,9,9,10,10-hexadecafluorodecane.

* * * * *